United States Patent [19]

Rosenwald

[11] Patent Number: 5,496,358
[45] Date of Patent: Mar. 5, 1996

[54] THERMAL WRAP FOR A BODY MEMBER

[75] Inventor: Mark A. Rosenwald, Chicago, Ill.

[73] Assignee: Sport Wrapz, Inc., Chicago, Ill.

[21] Appl. No.: 383,958

[22] Filed: Feb. 6, 1995

Related U.S. Application Data

[63] Continuation-in-part of Ser. No. 76,157, Jun. 14, 1993, Pat. No. 5,395,399.

[51] Int. Cl.$^6$ ............................................. A61F 7/00
[52] U.S. Cl. ..................... 607/108; 607/111; 607/112; 607/114; 126/204; 165/46
[58] Field of Search ........................ 607/108–112, 114; 126/204; 165/46; 62/530; 383/901

[56] References Cited

U.S. PATENT DOCUMENTS

| | | |
|---|---|---|
| 2,949,914 | 8/1958 | Waldrum . |
| 4,527,566 | 7/1985 | Abare . |
| 4,628,932 | 12/1986 | Tampa . |
| 4,641,655 | 2/1987 | Abt . |
| 4,688,572 | 8/1987 | Hubbard et al. . |
| 4,776,042 | 10/1988 | Hanson et al. . |
| 4,805,619 | 2/1989 | Swearingen . |
| 4,805,620 | 2/1989 | Meistrell ................................. 607/112 |
| 4,899,749 | 2/1990 | Laroco . |
| 4,972,832 | 11/1990 | Trapini et al. . |
| 4,976,262 | 12/1990 | Palmacci . |
| 5,020,711 | 6/1991 | Kelley . |
| 5,062,414 | 11/1991 | Grim . |
| 5,074,300 | 12/1991 | Murphy . |
| 5,148,804 | 9/1992 | Hill et al. . |
| 5,184,613 | 2/1993 | Mintz ...................................... 607/114 |
| 5,230,335 | 7/1993 | Johnson Jr. et al. ................... 607/108 |

Primary Examiner—Angela D. Sykes
Assistant Examiner—Robert L. Nasser, Jr.
Attorney, Agent, or Firm—Reising, Ethington, Barnard & Perry

[57] ABSTRACT

A thermal wrap is disclosed for application to body members, especially joints and limbs. It comprises a pouch for containing a thermal medium and which is constructed of a flexible elastic cloth. The pouch is mounted on a support member, also constructed of a flexible elastic cloth, which is adapted to wrap around a limb or joint. The support member is provided with a wrap fastener such as a hook and loop fastener which is adjustable to establish the desired degree of compression on the affected area. The wrap as applied to a knee and wrist is provided with cinch bands which encircle the limb at locations above and below the pouch. This arrangement provides compression under the bandwidth of the pouch which is independently adjustable relative to the compression under the cinch bands. Additionally, a pressurized air bladder may be provided to independently adjust the compression under the bandwidth of the pouch. Other advantageous features of the wrap that specifically relate to thermal wrapping an ankle and shoulder are also disclosed.

1 Claim, 8 Drawing Sheets

THERMAL WRAP FOR A BODY MEMBER

This is a continuation-in-part of U.S. patent application Ser. No. 08/076,157 filed Jun. 14, 1993 now U.S. Pat. No. 5,395,399.

FIELD OF THE INVENTION

This invention relates to thermal wraps useful for applying heat or cold to a member of the body. It is useful for either therapeutic or preventive treatment.

BACKGROUND OF THE INVENTION

There is a need for a thermal wrap which will effectively apply heat or cold to a limb, joint or other body member and also permit mobility with minimal encumbrance of freedom of movement. The thermal wrap must be easy to apply with a desired tightness. Further, it must be comfortable for the user and should allow vigorous activity of the body without becoming displaced from the affected area. It should, for example, withstand athletic activity such as running and skiing and also be suitable for a sedentary user. Further, the thermal wrap should be of low cost and it should accept a thermal medium for either cold or hot treatment. The thermal wrap should also be durable and reusable and preferably it should be made of breathable material.

It is well known that the application of heat or cold provides effective therapy for muscle and joint injuries. When properly applied, a thermal wrap is effective to provide pain relief from sprains, strains, bruises, muscle trauma and other injuries to the body. For effectiveness, the thermal wrap should provide intimate engagement of the thermal medium, whether hot or cold, with the affected area to obtain optimum heat transfer. In some applications, a controlled degree of compression on the affected area is desirable for enhancing the therapeutic effect.

Thermal wraps of wide variety have been proposed in the prior art. However, none has satisfactorily met the needs for a thermal wrap in regard to therapeutic effectiveness together with ease of use and mobility, as discussed above.

The Palmacci U.S. Pat. No. 4,976,262 granted Dec. 11, 1990 discloses an ice bag holding device especially adapted for application to the knee. This thermal wrap holds an ice bag of special design against the affected area by wrapping it around the knee joint and uses hook and loop fasteners for holding it in a stretched condition. The wrap is constructed of a stretchable material.

The Tampa U.S. Pat. No. 4,628,932 granted Dec. 16, 1986 discloses a knee ice pack which is wrapped around the knee and fastened with hook and loop fasteners. Waterproof compartments for holding ice are provided with a zipper closure at the top.

The Hubbard et al. U.S. Pat. No. 4,688,572 granted Aug. 25, 1987 discloses a thermal pack for application to the knee. This thermal pack comprises first and second pockets for holding thermal material which are connected together by a stretchable section. The thermal pack is wrapped around the knee with the stretchable section over the knee cap and held in place by straps in the region of the pockets which are secured by hook and loop fasteners.

Other prior art devices are described in the following patents: Murphy U.S. Pat. No. 5,074,300 granted Dec. 24, 1991 for "Reusable Fabric-Covered Heat-Exchange Bag"; Laroco U.S. Pat. No. 4,899,749 granted Feb. 13, 1990 for "Thermal Vascular Dilating Device And Method"; Swearingen U.S. Pat. No. 4,805,619 granted Feb. 24, 1989 for "Therapeutic Cooling Scarf, Wrap Or Collar"; Hanson et al. U.S. Pat. No. 4,776,042 granted Oct. 11, 1988 for "Cryokenetic Headband"; Abt U.S. Pat. No. 4,641,655 granted Feb. 10, 1987 for "Therapeutic Cooling Wrap"; and Waldrum U.S. Pat. No. 2,949,914 granted Aug. 23, 1960 for "Ankle Ice Pack".

A general object of this invention is to provide an improved thermal wrap which overcomes certain disadvantages of the prior art.

SUMMARY OF THE INVENTION

This invention provides a thermal wrap which is easy to use and which allows for mobility including vigorous activity without unwanted displacement while providing effective therapy to the affected area.

In accordance with the invention, this is provided by a thermal wrap comprising a flexible pouch for containing a thermal medium with a fastener system which keeps the pouch in place over the affected area with a controlled degree of compression on the affected area. A wrap fastener is effective over the pouch bandwidth to establish the amount of compression applied to the affected area and one or more adjustable cinch bands, which engage the body member remote from the affected area, apply an adjustable amount of holding force independently of the compression applied over the pouch bandwidth.

Further, in accordance with this invention, a controlled compression may be applied to the affected area independently of the tightness of the cinch bands. This is accomplished by an air bladder overlying the thermal pouch which may be pressurized to obtain the desired degree of compression applied directly to the affected area under the pouch.

These and other features, advantages and objects of the thermal wrap of the present invention will become more apparent from the preferred embodiments of the thermal wrap as specifically applied to various joints of the body including wrist, knee, ankle and shoulder and wherein a complete understanding of this invention may be obtained from the detailed description that follows taken with the accompanying drawings.

BEST MODE FOR CARRYING OUT THE INVENTION

Referring now to the drawings, illustrative embodiments of the invention are shown in a thermal wrap for therapeutic use on a limb or joint of a person. The thermal wraps shown will be described for application to joints of the body. It will be appreciated, as the description proceeds, that the invention is adapted for a variety of applications and may be realized in other embodiments.

Before describing the structure of the thermal wrap in a specific application, the concept, principles of construction and application of the invention will be described with reference to FIGS. 1 and 2. These figures are a schematic representation of the invention and illustrate the function of the main structural parts and also illustrate the relative forces which may be obtained in use of the invention.

Figure 1:
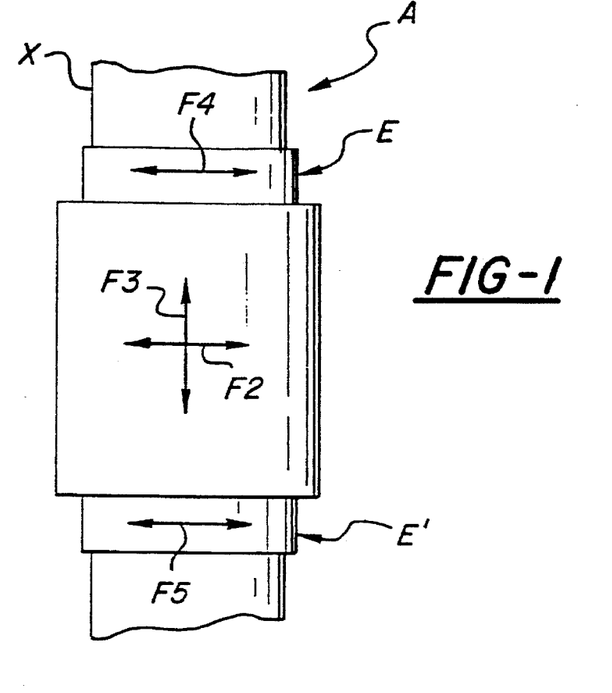
FIG. 1 is a schematic representation of the thermal wrap in a frontal view.
Figure 2:
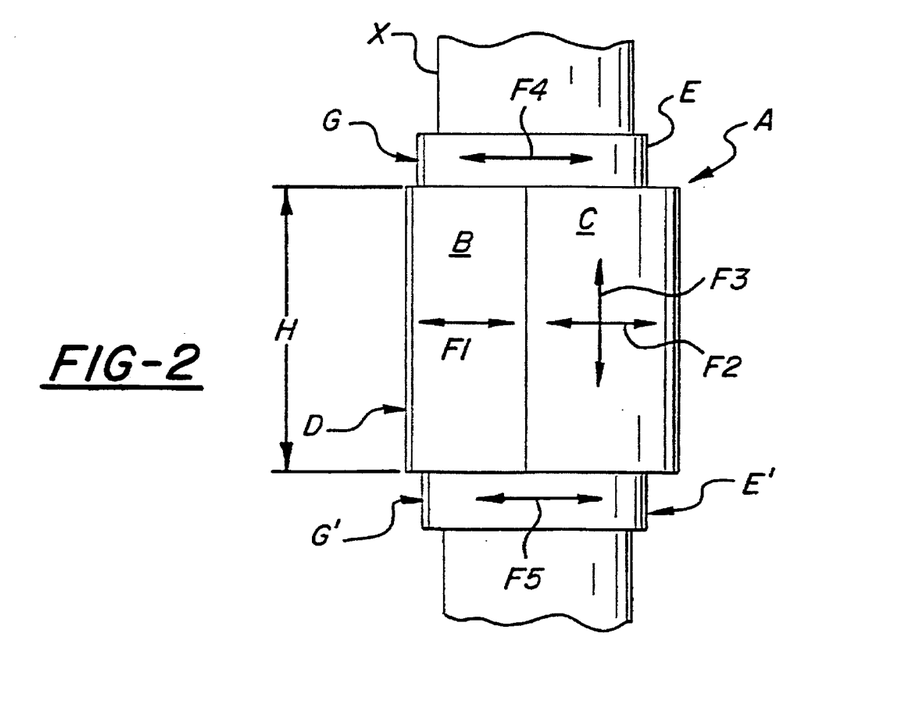
FIG. 2 is a side view of the thermal wrap of FIG. 1.

In the schematic drawings of FIGS. 1 and 2, a persons limb, e.g. leg, is represented by a cylindrical member X and is shown in front and side views. The thermal wrap A of this invention is applied to the limb by wrapping it around the limb and fastening it in place. The thermal wrap A comprises a support member B which is constructed of a generally rectangular flexible elastic sheet. A pouch C is mounted on the support member B and has inner and outer walls or panels each of which is constructed of a flexible elastic sheet. The outer panel is attached around its periphery to the support member and the underlying portion of the support member constitutes the inner panel. The pouch C is adapted to contain a thermal medium such as ice or a sealed gel package, and is provided with an opening and suitable closure for inserting and removing the thermal medium.

For application of the thermal wrap A to the limb, the support member B is wrapped around the limb in a single layer except for overlapping of the lateral edges by an amount depending upon the lateral dimensions. Preferably, the medium is inserted into the pouch C prior to wrapping. The wrap is positioned circumferentially on the limb so that the pouch C overlies the affected area to be treated. The amount of radial compression to be exerted by the wrap on the affected area of the limb is determined by the adjustment of an adjustable wrap fastener D which is engaged and tightened as desired when the wrap is applied and which is readjustable afterward. Preferably, the wrap fastener D is adapted for establishing substantially uniform tension in the support member B throughout a bandwidth H having a dimension about the same as the vertical length of the pouch C (herein called the "pouch bandwidth").

In order to secure the thermal wrap A in place on the limb so that it remains substantially fixed despite movement of the limb, an upper anchor or cinch band E is provided and preferably, but optionally, a lower cinch band E' is provided. The cinch bands E and E' are provided, respectively, with fasteners G and G' which are individually adjustable to establish the tension in the cinch bands E and E', respectively. Each of the cinch bands E and E' may be constructed of an axial extension of the support member B with a strap secured to and partially overlapping the extension. Each of the cinch bands E and E' may be provided with an elastic section which has an elasticity different from that of the remainder of the band.

The use of the thermal wrap depicted in FIGS. 1 and 2 will now be described with reference to the stresses in and the forces exerted by different parts of the wrap. A tensile stress F1 is established in the support member B and is substantially uniform in the pouch bandwidth. This tensile stress F1 is determined by the amount the support member B is stretched when the fastener D is secured. This tensile stress F1 is effective to apply a radial compressive force over the encircled portion of the limb and may be adjusted to suit the needs of the user. There is also a tensile stress F2 in the circumferential direction in the outer panel of the pouch C. The tensile stress F2 will be greater or lesser than the tensile stress F1 depending upon the elasticity of the outer panel relative to the inner panel and depending upon the amount of stretching of the outer panel due to the filling of the pouch C with a thermal medium. There will also be an axial stress F3 in the outer panel of the pouch due to the filling of the pouch. These stresses in the outer panel, especially the stress F2, and hence the radial compression applied thereby are of importance in the use of the thermal wrap because it may increase the radial compression force applied to the affected areas of the limb. If the thermal medium is granular or chunky, such as ice, a comfort factor may be involved.

As discussed above, the wrap A is held in a wrapped condition around the limb by the fastener D. The compressional force exerted by the wrap on the limb over the pouch bandwidth, may be adjusted from substantially zero to a relatively large value. This radial compression does tend to hold the thermal wrap in place but additional holding is required depending upon the expected activity of the limb. This is provided by the cinch bands E and E', at least one of which is required. If only one is used, it is preferably the upper cinch band E and, for a greater holding effect, both are preferably used. The tensile stress F4 in the cinch band E is established by the amount of stretch in the band E when the fastener G is secured. The same is true of the tensile stress F5 in the band E'. In the respective cinch bands E and E', the tensile stresses F4 and F5 are independently adjustable and determine, respectively, the radially extending compressive forces on the limb and hence, the holding force of each.

It is especially noteworthy that the compressive force applied to the affected area of the limb, i.e. under the pouch bandwidth, is adjustable independently of the holding force provided by the cinch bands. Further, the compression applied under the pouch may be different from the compression applied under the remainder of the pouch bandwidth, depending upon the construction of the pouch. This independent relationship between the compression on the affected area by the pouch bandwidth and that under the cinch bands is extremely important in the use of the thermal wrap. It allows the thermal treatment of the affected area to be optimized by establishing the compression in the pouch bandwidth in accordance with the condition of the affected area. This compression may range from substantially zero to a relatively high value. At the same time, the radial compression established in the upper and lower cinch bands may be adjusted independently of the pouch bandwidth and independently of each other. This combination enables the optimum treatment of the affected area with a selected compression while permitting the holding force of the thermal wrap to be adjusted in accordance with the desired degree of activity of the limb. Thus, the effectiveness of the thermal wrap may be maximized while the mobility and the comfort of the user are also maximized.

Preferred Embodiments

In view of the foregoing discussion of the thermal wrap of this invention, several different embodiments and the details of construction will now be described setting forth the best mode now contemplated for carrying out the invention.

The Knee Wrap (First Embodiment)

Figure 3:
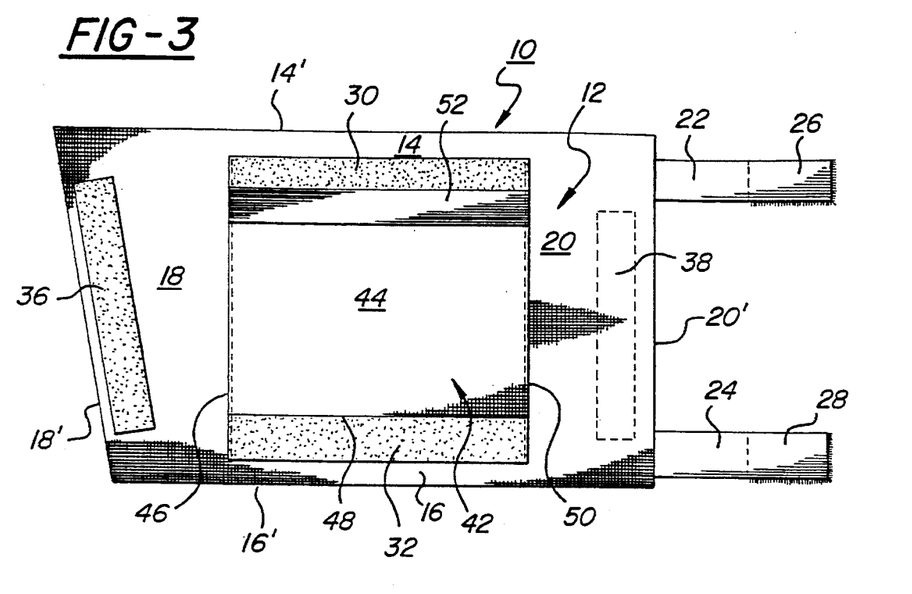
FIG. 3 is a view of the knee wrap showing the outer surface laid flat.
Figure 4:
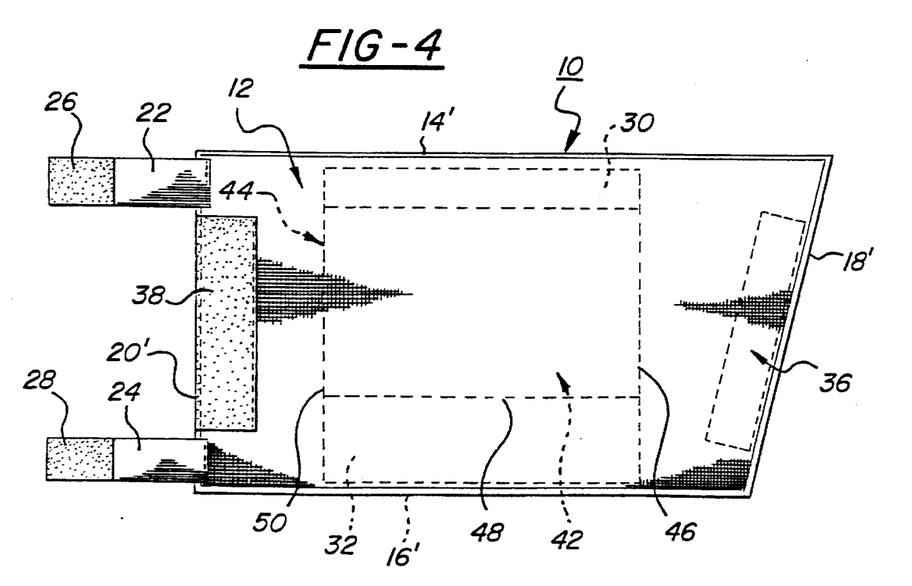
FIG. 4 shows the inner surface of the wrap of FIG. 3.
Figure 5:
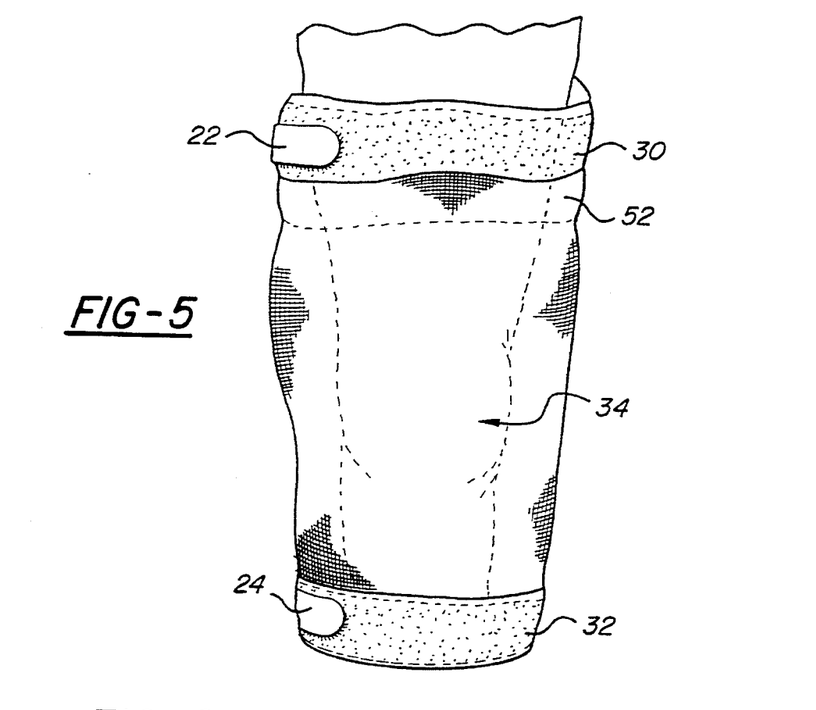
FIG. 5 shows the knee wrap in place on a person's knee.

Referring now to FIGS. 3, 4 and 5, the invention will now be described in a knee wrap application.

The knee wrap 10 comprises, in general, a support member 12 which carries a flexible pouch 42 having a pouch wall or panel 44 secured to the support member 12. The placement of the pouch panel 44 on the support member 12 provides a top border 14 between the top edge 14' and the pouch and it also provides a bottom border 16 between the bottom edge 16' and the pouch. Similarly, it provides a left side border 18 and a right side border 20 between the side edges 18' and 20', respectively. The support member 12 is provided with a compression adjustment or wrap fastener which comprises first and second coacting parts 36 and 38. It is also provided with upper and lower flexible straps 22 and 24, respectively, which form a part of the upper and lower cinch bands. Upper and lower cinch band fasteners comprise, respectively, coacting parts 22 and 36 for the upper fastener and parts 24 and 36 for the lower fastener. The wrap 10 is shown in FIG. 5 as it appears when it is applied by wrapping around a person's knee 34.

The structure of the knee wrap of FIGS. 3–5 will now be described in more detail. The support member 12 comprises a flexible elastic sheet of cloth which is generally rectangular in shape and suitably trapezoidal to account for the diminishing diameter of the leg area from above the knee joint to below it. The support member is dimensioned from top to bottom so as to cover the knee and from side-to-side so as to permit wrapping of a single layer around the knee joint with some overlap of the fastener parts 36–38. The cloth of the support member 12 is preferably a stretch fabric such as those sold under the names "Darlexx"™, "Lycra"™ or "Spandex"™ which provide omnidirectional elasticity. In some applications, the cloth may be "Neoprene™" rubber or it may be a paper-like material with a plastic coating or binder as "Tyvek"™ (a trademark of Dupont) which is made of one hundred percent high density polyethylene fillers and binders (Hdep-2). The edges 14', 16', 18' and 20' of the support member 12 are folded over upon themselves and joined to the support member 12 along a line by stitching (not shown) to form a double layer.

The flexible pouch 42 comprises the outer pouch panel 44 which is disposed in face-to-face relation with a central portion of the support member 12 and is joined thereto by stitching 46, 48 and 50. The pouch panel 44 is preferably joined, as described, to the support member 12 with both of them in an unstressed condition to form an expandable pouch which is formed by the outer panel 44 and an inner panel which comprises the facing portion of the support member 12. The pouch has an opening at the upper edge in the region between the stitching 46 and 50 for insertion and removal of the thermal medium. The panel 44 is preferably constructed of the same material as support member 12. A closure is provided for the opening to ensure containment of the thermal medium. This closure comprises a two-part fastener of the hook and loop type and comprises coacting fastener strips 30 and 52. The fastener strip 30 extends across the top of the pouch and is mounted on the support member 12 as by stitching (not shown). The fastener strip 52 is mounted on the inner side of the panel 44 and extends across the opening but is of narrower width than the strip 30. This leaves the upper portion of the fastener strip 30 exposed for a purpose which will be described below.

The wrap fastener for securing the overlapping ends of wrap together comprises a hook and loop fastener with the fastener strips 36 and 38. The fastener strip 36 is mounted on the left side border 18 substantially parallel to the left side edge 18' on the outer face of the support member 12. The coacting fastener strip 38 is mounted on the border 20 substantially parallel to the right side edge 20' and on the inner face of the support member 12.

For securing the thermal wrap in place on the limb, the upper cinch band is provided which comprises the flexible elastic strap 22 and the upper border 14 of the support member 12. The strap 22 is secured by stitching at one end to the right side border 20 in alignment with the upper border 14. Similarly, the lower cinch band comprises an flexible elastic strap 24 and the lower border 16 of the support member 12. The strap 24 is secured by stitching to the right side border 20 in alignment with the lower border 16. An adjustable fastener for the upper cinch band is provided by a hook and loop fastener comprising a fastener patch 26 and a coacting strip 30. The patch 26 is mounted by stitching on the free end of the support strap 22. Similarly, an adjustable hook and loop fastener is provided for the lower cinch band and comprises a patch 28 mounted on the free end of support strap 24 and a coacting strip 32 mounted on the exposed face of the pouch panel 44 by stitching.

The fasteners referred to above as hook and loop fasteners are of the type sold under the name "Velcro™". It will be understood that other fasteners which provide adjustability may be used for the cinch and wrap fasteners such as strap-and-buckle fasteners, snap fasteners and tie strings and such others as will occur to those skilled in the art. Other closure fasteners for the pouch include plastic zip-lock fasteners (like foodbag closures), zippers and such other devices as will occur to those skilled in the art.

The pouch 42 is adapted to receive a thermal medium such as ice, hot water, pre-packaged gels and anti-freeze liquids. Preferably, the thermal medium is a pre-packaged gel of the type which may be heated or chilled and is flexible even when chilled.

For use with the pre-packaged thermal material, the pouch of the thermal wrap does not need to be waterproof. However, if the pouch is to be filled with ice or water, waterproof construction is required. Waterproof construction may be provided by using a waterproof material for the support member 12 such as "Darlexx"™, rubber or "Tyvek"™ referred to above. Depending upon the materials selected for the pouch panel 44 and the support member 12, the joinder therebetween along the lines 46, 48 and 50 may be provided by known techniques such as thermal welding, laser welding, laser enhanced bonding or heat staking. For a waterproof pouch, the closure fastener may be provided by a water-tight zipper or a plastic zip lock. One example of a preferred material for a waterproof pouch uses "Darlexx"™ style 3650 (available from Darlington Fabrics Corp., New York, N.Y.) for both the support member 12 and the pouch panel 44. The seams are formed by laser enhanced bonding, a process by which a laser beam drives a polymer adhesive bonding agent into the materials being joined. This process is available from Lightseam Technologies, Inc. of Golden, Colo. Also the seams of "Darlexx"™ may be formed by liquid adhesive such as GE Primer 118 and GE Silicon 4179 available from General Electric Company of Schenectady, N.Y. Also, seams may be formed by composite tapes having a thermoplastic adhesive layer and an outer layer for abrasion resistance and appearance such as that available from Electro-Seal Corporation or Mann Industries. Such seam tapes can be applied with hot-air sealers available from Pfaff Corporation.

The Knee Wrap (Second Embodiment)

Figure 6:
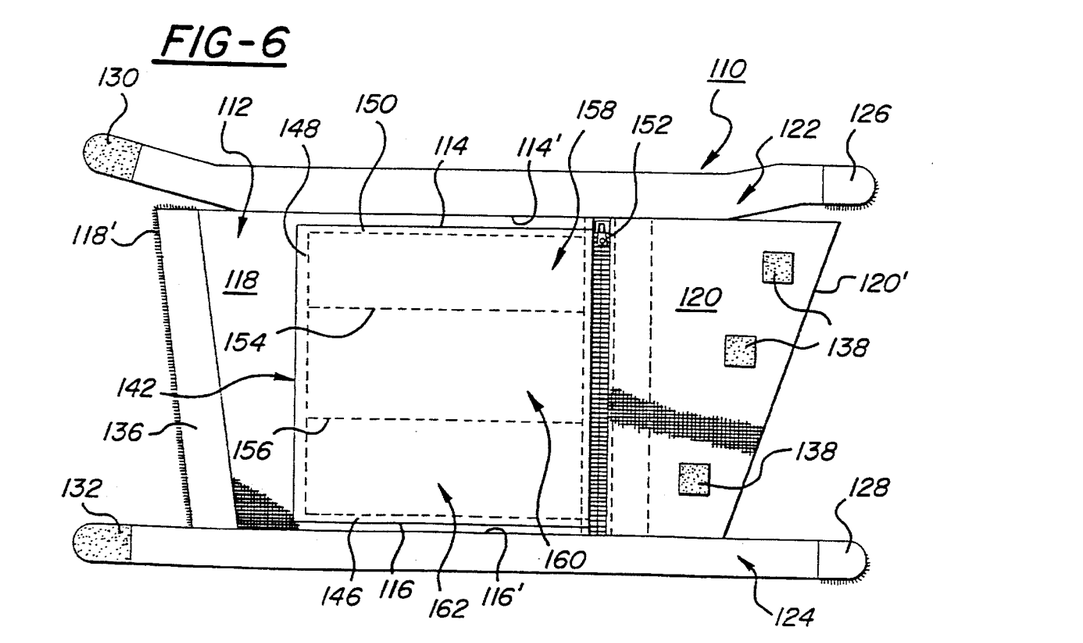
FIG. 6 shows a second embodiment of the knee wrap.

A second embodiment of the knee wrap is shown in FIG. 6 and is similar to that of FIGS. 3, 4 and 5. In the description of this embodiment, the reference numbers used in FIG. 6 for parts which correspond to parts in FIGS. 3, 4 and 5, are greater by one hundred than the numbers in FIGS. 3, 4 and 5.

Referring now to FIG. 6, the construction of the support member 112 is similar to support member 12 of the first embodiment and differs in that the upper and lower borders 114 and 116 are relatively narrower and the upper and lower cinch bands comprise separate straps 122 and 124. The straps are joined to the support member 112 by stitching and are constructed of a less easily stretched material (i.e. having a higher stretch modulus of elasticity) than material of the support member. The strap 122 is provided with a hook and loop fastener comprising a patch 126 mounted on one end of the strap and a coating patch on the other end. Similarly, the strap 124 is provided with a fastener comprising a patch 128 mounted on one end and a coating patch 132 mounted on the other end.

The pouch panel 144 is of the same construction as the pouch panel 44 of the first embodiment except that the opening is provided on the side of the pouch 142 and the closure fastener comprises a zipper 152. A further difference is that the pouch 142 is divided into plural compartments 158, 160 and 162 by a pair of joinder lines connecting the panel 144 to the support member 120 which are provided by stitching 154 and 156. This arrangement is especially useful for a thermal medium of flowable constituency such as granular, gel or liquid material to ensure an even distribution thereof over the affected area.

The second embodiment, as shown in FIG. 6, is provided with a wrap fastener similar to that of the first embodiment. It differs in that discrete fastener patches 138 (instead of a continuous strip 38) are mounted on the right hand border 120 for coacting with the velcro strip 136 on the left hand border 118.

The second embodiment, may have a non-waterproof pouch or a waterproof pouch by selection of the appropriate materials and parts as discussed above.

The Knee Wrap (Third Embodiment)

Figure 7:
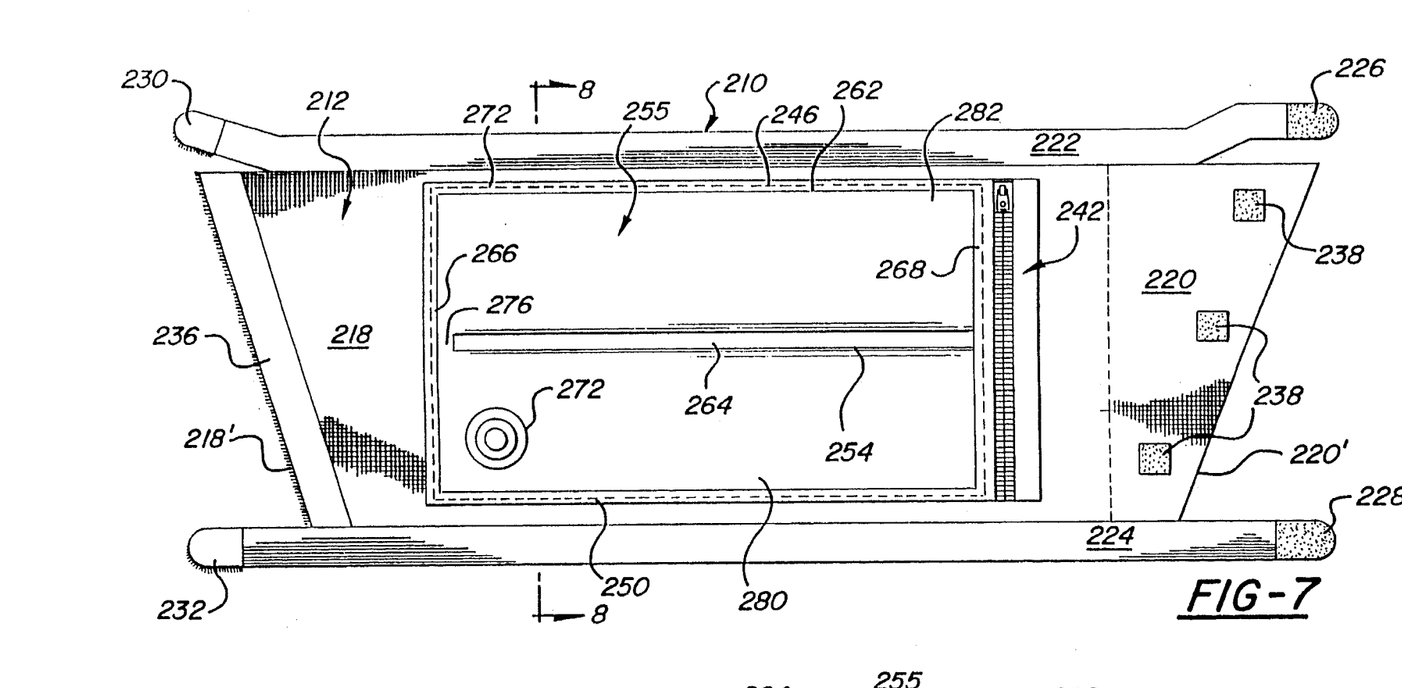
FIG. 7 shows a third embodiment of the knee wrap with an air bladder for compression control.
Figure 8:
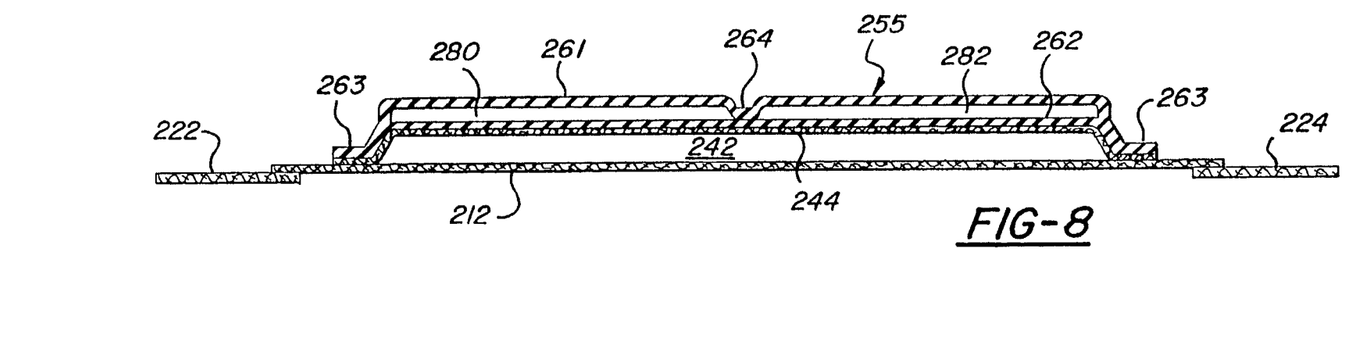
FIG. 8 is a cross-sectional view taken on lines 8—8 of FIG. 7.

A third embodiment of the invention in a knee wrap is shown in FIGS. 7 and 8. This embodiment is like the second embodiment except that a pressurized air bladder is added for adjustment of the radial compression applied to the affected area. In this embodiment, those parts which correspond to similar parts in the second embodiment are referred to by the same reference numbers except that the first digit is "2" instead of "1". The construction of the support member 212, the thermal medium pouch 242 and the fasteners are the same as in the second embodiment. The difference is that the air bladder 255 is superimposed on the pouch 242.

The air bladder 255 comprises a thin airtight flexible elastic bladder joined around its periphery to the panel 244 to provide an airtight enclosure. Preferably, the bladder material has a much higher stretch modulus than panel 244. The bladder 255 has outer and inner walls 261 and 262 which are joined at their peripheral edges to form a flange 263. It is suitably constructed of rubber and the seams may be formed by vulcanizing. The flange which encircles the bladder serves for securement to the panel 244 and support member 212. For this purpose, the flange 263 is joined by stitching 246 and 250 along its upper and lower edges, respectively, to the panel 244 and the support member 212; is joined by stitching 266 and 268, along its sides to the panel 244 and support member 212. Additionally, the walls 261 and 262 of the bladder are joined together by a joint 264 which provides side-by-side bladder compartments 280 and 282. The joint 264 has one end 276 spaced from the end of the bladder to provide an air passage between the compartments 280 and 282. The joint 264 restricts the bulging of the panel 262 and the deformation of the panel 244 which might otherwise occur. The joint 264 also facilitates bending of the wrap along the line of the joint and minimizes interference with the flexing of the knee being treated.

In order to pressurize the air bladder 255, an air pump 272 is built into the air bladder 255, as shown in the lower left hand corner of the air bladder. The pump 272 is manually actuated by a finger or thumb to pump air into the bladder and is manually actuated to release pressure as desired. The pump 272 is like that used in the high top basketball shoes sold by Reebok and known as "THE PUMP"™. Obviously, a pump which is separate and detachable from the thermal wrap may be used if desired. Such a pump, with a suitable valve in the bladder, may be like those used for inflating basketballs and footballs.

When the air bladder 255 is not pressurized, the thermal wrap 210 functions in the same manner as the thermal wrap 110. When the air bladder 255 is pressurized, the wrap fastener, comprising fastener parts 236 and 238, is tightened and the air bladder expands against the pouch 242 and increases the compressive force applied to the limb.

The Wrist Wrap

Figure 9:
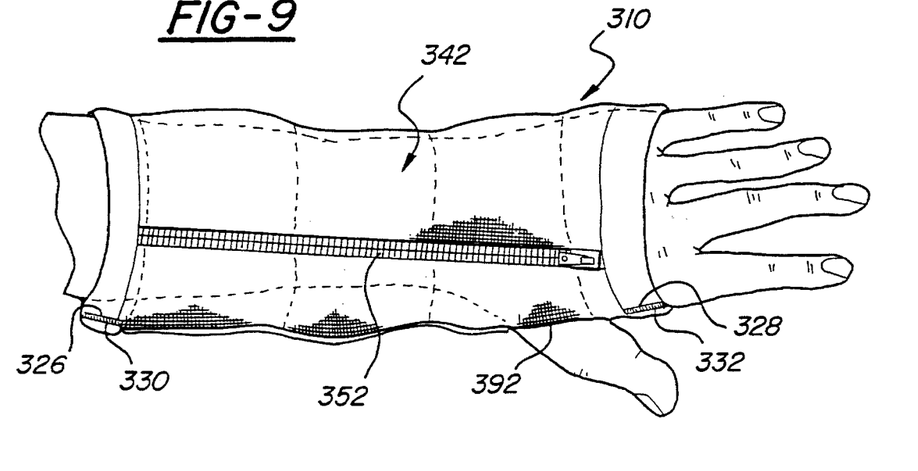
FIG. 9 illustrates a wrist wrap in place on a person's wrist.
Figure 10:
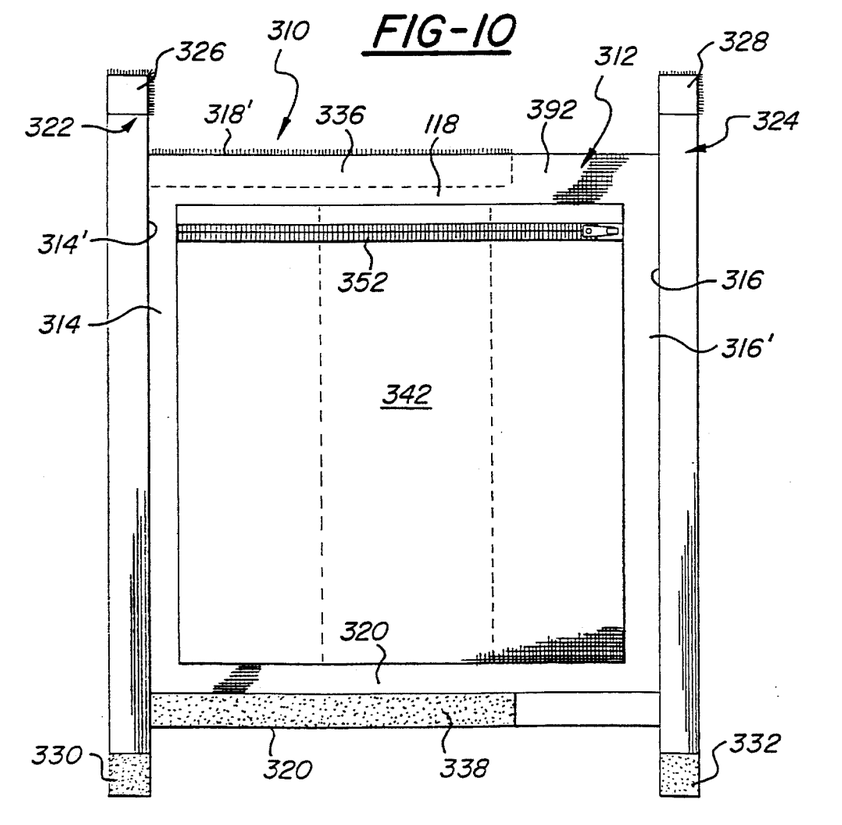
FIG. 10 shows the wrist wrap in a view of the outer surface laid flat.

An embodiment of the invention for use as a thermal wrap for a wrist is shown in FIGS. 9 and 10. It is similar to the second embodiment of the knee wrap shown in FIG. 6. In FIGS. 9 and 10, those parts which correspond to similar parts in FIG. 6 are referred to by the same reference numbers except that the first digit is "3" instead of "1".

Referring now to FIGS. 9 and 10, the construction of the support member 312 is similar to support member 112 of FIG. 6 except that it is rectangular instead of trapezoidal.

The pouch 342, the cinch bands comprising straps 322 and 324, and the cinch band fastener parts 326–330 and 328–332 are the same as FIG. 6.

The wrap fastener is similar to that of FIG. 6 except that the hook and loop fastener strips 336 and 338 do not extend the full width of the pouch 342 thereby leaving an opening in the wrap for the thumb of the user.

As illustrated in FIG. 9, the wrist wrap is applied to the wrist by wrapping it around the lower arm and wrist with the thumb extending through the opening 392 and engaging the wrap fastener parts 336 and 338. Then, the lower strap 324 is pulled to the desired tightness around the hand and the cinch band fastener parts 328–332 are engaged. Finally, the cinch band comprising strap 322 is tightened as desired around the arm and the cinch band fastener parts 326 and 330 are engaged.

The Ankle Wrap

Figure 13:
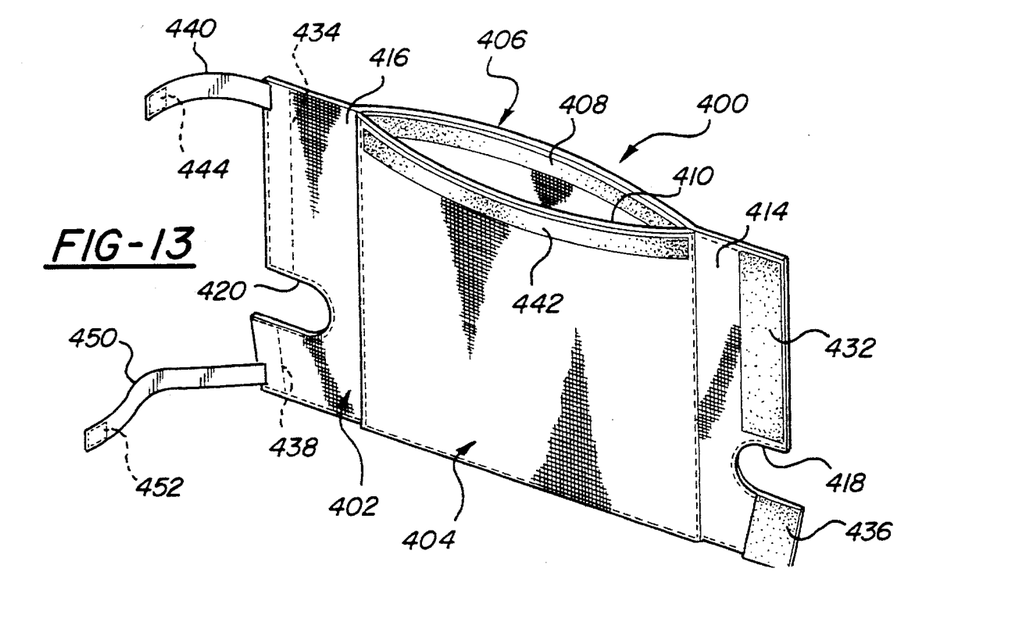
FIG. 13 is a perspective view of the ankle wrap.

An embodiment of the invention for use as a thermal wrap for an ankle is shown in FIGS. 11–15 and is generally designated as 400. The ankle wrap 400 like in the previously described embodiments includes flexible elastic cloth members or panels 402 and 404 that are stitched together so as to co-operatively define a flexible elastic pouch 406 that is adapted to receive a thermal medium. The latter is retained in the pouch by hook and loop fastener strips 408 and 410 stitched to the opposite inner sides of the top of the pouch as seen in FIG. 13.

Figure 14:
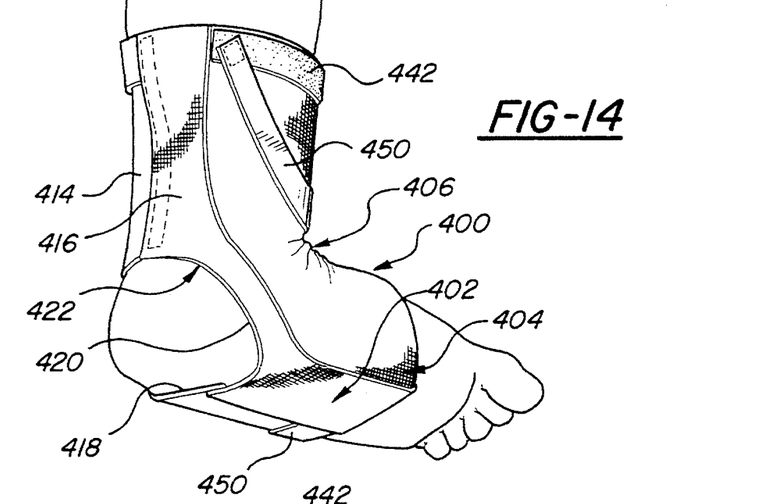
FIG. 14 is a view showing the ankle wrap in place on a person's ankle when looking from a rear view point.
Figure 15:
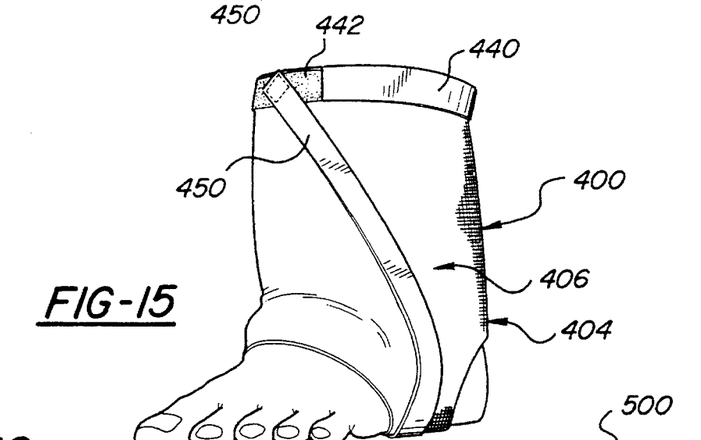
FIG. 15 is view like FIG. 14 but from a frontal view point.

The ankle wrap 400 is adapted to be wrapped partially about a lower leg region and an ankle and an upper foot region of a person as shown in FIGS. 14 and 15 and provide adjustable pressure of the pouch against the ankle as will now be described.

The inner elastic cloth panel 402 includes a first flexible elastic border portion 414 extending along one lateral side of the pouch and a second flexible elastic border portion 416 extending along an opposite lateral side of the pouch. The border portions 414 and 416 are adapted to be brought together in an overlapping relationship in locations behind the lower leg region and under a midportion of the foot when the pouch is wrapped about the lower leg region and ankle and upper foot region as shown in FIGS. 14 and 15.

Figures 11, 12:
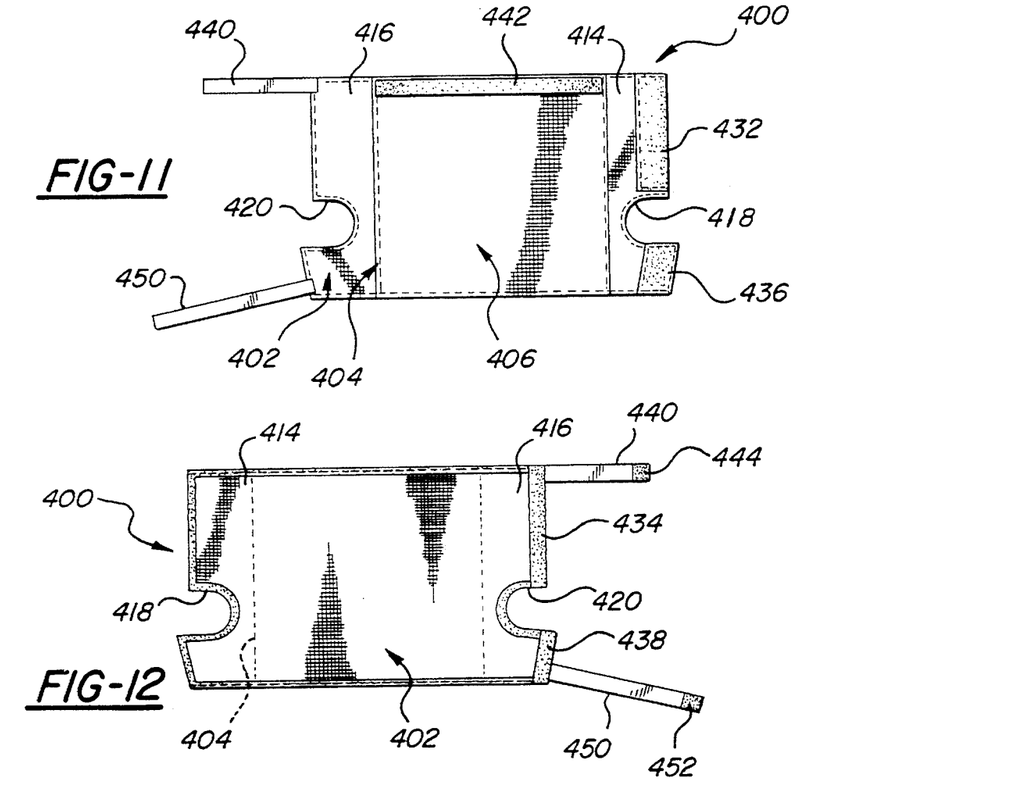
FIG. 11 is a view of an ankle wrap according to the invention laid flat with its outer side facing outward.
FIG. 12 is a view of the inner side of the ankle wrap.

A gap 418 and 420 is provided in the respective border portions 414 and 416 at a location about one-third of the length of the wrap from the bottom as viewed in FIGS. 11–13 and these gaps co-operatively define an opening 422 of generally circular shape in these border portions adapted to receive the heel of the foot when the pouch 406 is wrapped about the lower leg region and ankle and upper foot region and these border portions are brought in to overlapping relationship as shown in FIG. 14. A first wrap fastener comprising a hook and loop fastener strip 432 stitched to the outer side of the border portion 414 and a strip 434 of the same length but smaller width stitched to the inner side of the other border portion 416 provide for fastening these border portions together in overlapping relationship at a location above the heel opening 422 whereby an upper region of the pouch 406 is adapted to be held against the ankle with an adjustable tension force in this wrap fastener. A second wrap fastener of shorter length comprising a hook and loop fastener strip 436 stitched to the outer side of the border portion 414 and a strip 438 of the same length but smaller width stitched to the inner side of the other border portion 416 provide for fastening these border portions together in overlapping relationship at a location below the heel opening 422 whereby a lower region of the pouch 406 is adapted to be held against the ankle with an adjustable tension force in this wrap fastener that is independent of that applied by the other wrap fastener comprising the hook and loop fastener strips 432 and 434.

The ankle wrap is firmly held in place at a location above the ankle by an independently applied tension force provided by an elastic cinch strap 440 that is stitched at one end to the upper outer corner of the elastic border portion 416 and is of sufficient length to wrap about the lower leg region of a person at a location above the ankle. A cinch strap fastener is provided for fastening the cinch strap 440 to the upper transverse edge of the pouch after the cinch strap has been wrapped about the lower leg region and comprises a hook and loop fastener strip 442 and patch 444. The cinch strap fastener strip 442 extends along the length of and is stitched to the outer side of an upper transverse margin of the outer cloth member 404 of the pouch 406 and the cinch strap fastener patch 444 is stitched to the inner side of the distal end of the cinch strap 440. The cinch strap fastener strip 442 and patch 444 thus provide for fastening the cinch strap 440 so as to press the top of the pouch against the lower leg region at a location above the ankle with an adjustable tension force in the cinch strap fastener that is independent of that applied by either of the two wrap fasteners 432,434 and 436,438. The fastener strips are relatively inelastic and the stitching of the cinch strap fastener strip 442 to the top margin of the outer pouch panel 404 thus renders the latter relatively inelastic which is used to advantage in compressing the pouch against the ankle with a tensioning strap independent of the cinch strap and wrap fasteners as will now be described.

Further control or adjustment of the pressure of the thermal pouch against the ankle in addition to that provided by the single cinch strap and the two wrap fasteners is provided by an elastic tension strap 450. The tension strap 450 is stitched at one end to the outer side of the lower outer corner of the border 416 over the wrap fastener strip 438 that is located on the inner side. The tension strap 450 is provided with a length sufficient to extend diagonally across and over the pouch 406 to the upper transverse edge of the pouch as seen in FIG. 15. The tension strap 450 is adjustably attachable to the upper transverse edge of the outer panel 404 of the pouch by a tension strap fastener comprising a hook and loop fastener patch 452 that is stitched to the inner side of the distal end of the tension strap 450 and fastens to the hook and loop fastener strip 442 that also serves to fasten the cinch strap 440. The tension strap 450 is thus operatively connected to apply a force pressing the pouch against the ankle that is independent of that applied by both the cinch strap and the two wrap fasteners.

The ankle wrap is initially wrapped about and fastened in place with the two wrap fasteners 432,434 and 436,438 and the cinch strap 440 is then pulled around the lower leg portion and fastened above the ankle to the top of the pocket with the cinch strap fastener 442,444. The tension strap 450 is then pulled across and to the top of the pouch where it is fastened with the tension strap fastener 442, 452. And the compression of the pouch on the ankle may then be adjusted as desired by tightening or loosening the cinch strap 440 and the tension strap 450.

The Shoulder Wrap

An embodiment of the invention for use as a thermal wrap for a shoulder is shown in FIGS. 16–19 and is designated as 500. The shoulder wrap 500 like in the previously described embodiments includes flexible elastic cloth members or panels that are stitched together so as to co-operatively define a flexible elastic pouch. However, in this thermal wrap application there are provided two outer panels 502 and 504 that are stitched to a single inner panel 506 to form a double pouch 508 having a front compartment 510 with an opening 511 for receiving a thermal medium and an adjoining rear compartment 512 with an opening 513 for receiving another thermal medium. The thermal mediums are retained in the compartments by hook and loop fastener strips 514 and 516 that are stitched to the inner side of the top of the respective compartment outer panels 502 and 504 and fasten to a common hook and loop fastener strip 518 stitched to the inner panel 506 to close the respective openings 511 and 513.

Figure 19:
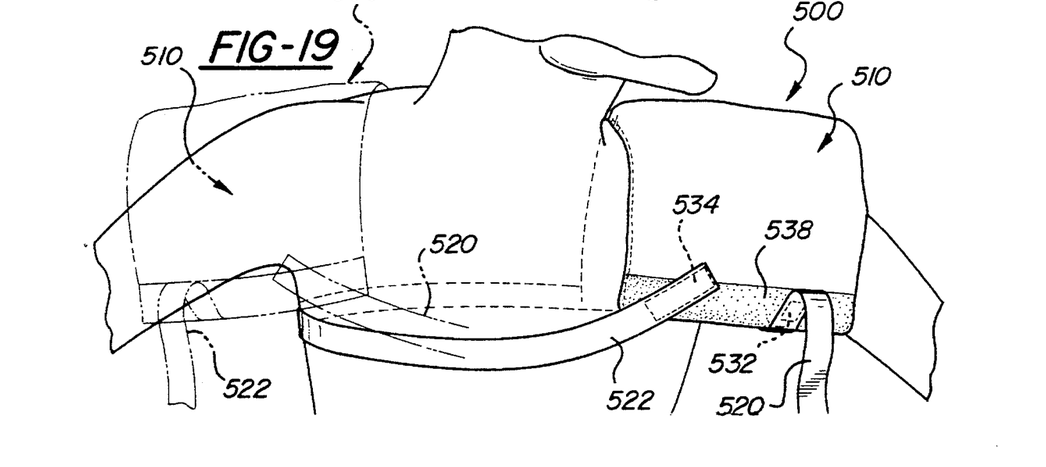
FIG. 19 shows the shoulder wrap in place on a person's shoulder and includes a phantom line view showing the same shoulder wrap in place on this person's other shoulder.

The shoulder wrap 500 is secured in place with two cinch straps 520 and 522 and is adapted to be draped over either shoulder of a person as illustrated in FIG. 19 with the front pouch compartment 510 always located at the front of the person and the rear pouch compartment 512 always located at the rear so as to position the cinch straps for quick and easy fastening of the shoulder wrap in place as will become more clear from the arrangement and fastening of the cinch straps 520 and 522. The cinch straps 520 and 522 are identical and are stitched at one end to the respective lower corners of the rear pouch compartment 512 and adjustably fasten to the front pouch compartment to hold the wrap in place.

Figure 16:
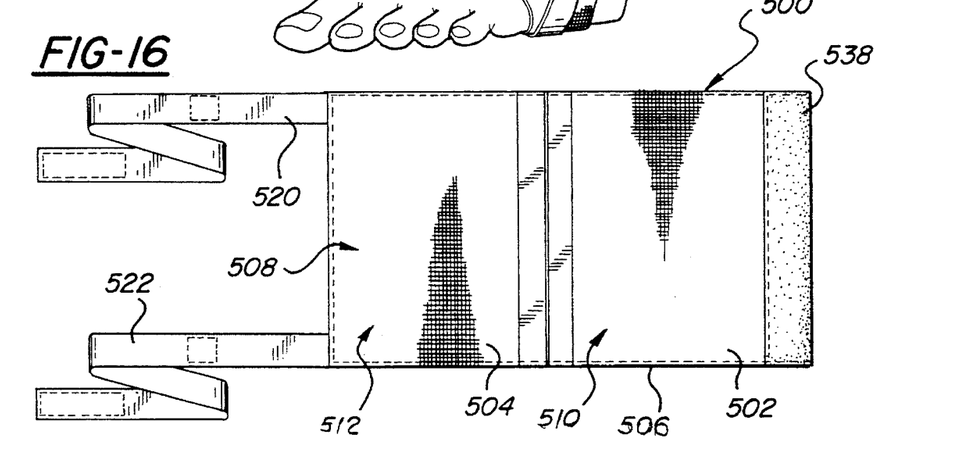
FIG. 16 is view of a shoulder wrap according to the invention laid flat with its outer side facing outward.
Figure 17:
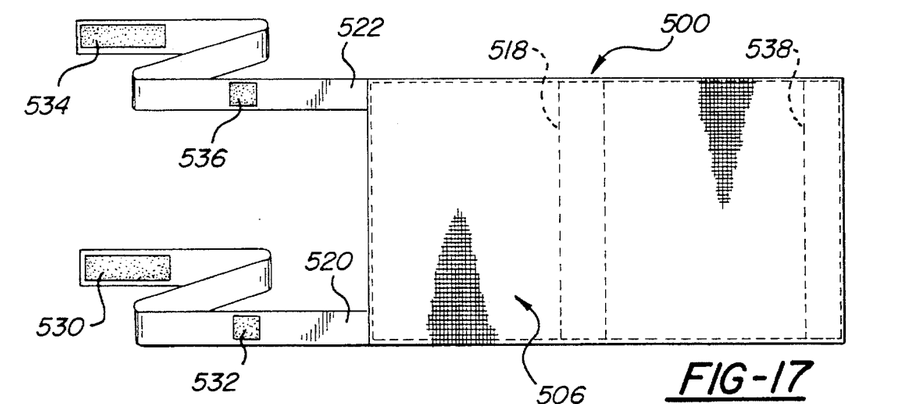
FIG. 17 is a view of the inner side of the shoulder wrap.
Figure 18:
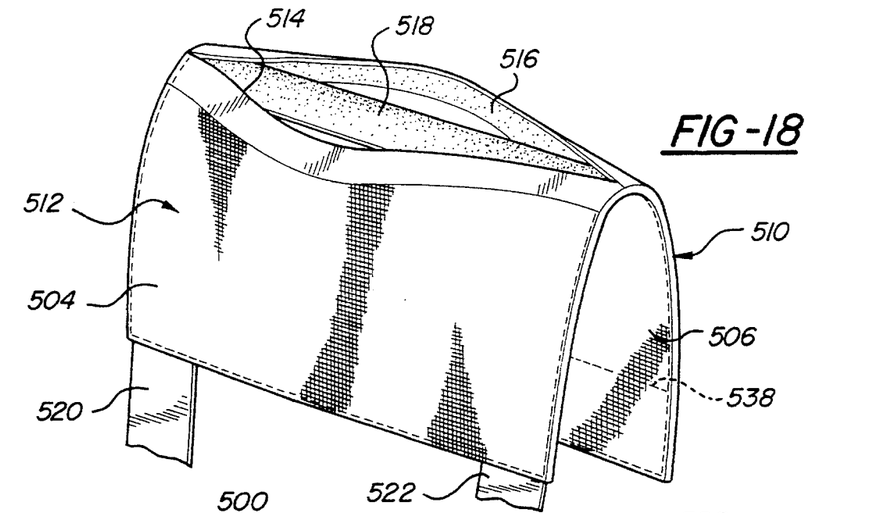
FIG. 18 is a perspective view of the shoulder wrap.

The fasteners for the cinch straps comprise a hook and loop fastener strip 530 and patch 532 that are stitched to the inner side of the cinch strap 520, a hook and loop fastener strip 534 and patch 536 that are stitched to the inner side of the other cinch strap 522 in the same relative locations, and a hook and loop fastener strip 538 that extends along the lower edge and is stitched to the outer side of the front compartment panel 502 along a lower margin thereof. The cinch strap fastener strip 538 on the front pouch compartment is common to all the cinch strap fasteners as it forms one of the two parts of each of the fasteners that adjustably connect the cinch straps to the pouch to hold the latter against the shoulder with adjustable tension forces as will now be described.

The fastener parts 530 and 534 are located at the distal ends of the respective cinch straps 520 and 522 and provide for fastening their respective cinch strap to the cinch fastener part 538 on the front pouch compartment when this cinch strap is wrapped or looped about the torso as described below. The other cinch fastener parts 532 and 536 on the cinch straps are located at an intermediate position on the cinch straps and provide for fastening their respective cinch strap to the cinch fastener part 538 on the front pouch compartment when this cinch strap is wrapped or looped about an arm as described below.

The cinch straps are of a sufficient length so that when the wrap 500 is for example draped over the right shoulder as seen in solid line in FIG. 19, the cinch strap 522 (which then may be referred to as the inside strap) is arrangeable to wrap over a relatively long length thereof in a looping direction partially about the torso of the person from the lower left corner of the rear pouch compartment 512 to the lower transverse edge of the front pouch compartment 510 where it is fastened with its distal fastener part 534 to the fastener part 538 on the front pouch compartment in a leftward location. And the other strap 520 (which may then be referred to as the outside strap) is then arrangeable to wrap over a relatively short length thereof partially about (under) the right arm of the person from the lower right corner of the rear pouch compartment to the lower edge of the front pouch compartment where it is fastened with its intermediately located fastener part 536 to the fastener part 538 on the front pouch compartment in a rightward location.

Alternatively, when the wrap 500 is draped over the left shoulder as shown in phantom line in FIG. 19, the cinch strap 520 is then the inside strap and is arrangeable to wrap over a relatively long length thereof in a looping direction partially about the torso of the person from the lower right corner of the rear pouch compartment to the lower edge of the front pouch compartment where it is fastened with its distal fastener part 530 to the fastener part 538 on the front pouch compartment in a rightward location. And the other strap 522 which is then the outside strap is then arrangeable to wrap over a relatively short length thereof partially about (under) the left arm from the lower left corner of the rear pouch compartment to the lower edge of the front pouch compartment where it is fastened with its fastener part 536 to the fastener part 538 on the front pouch compartment in a leftward location.

With the wrap 500 thus fastened in place on either shoulder, it will be appreciated that the outside cinch strap applies tension to press the wrap against the shoulder in the area adjacent the adjoining arm while the inside cinch strap applies tension independent of the outside strap to press the wrap against the shoulder in the area adjacent the neck. And these pressure forces can thus be readily adjusted independently of each other with the cinch strap fasteners while the wrap remains in place on the shoulder.

It will also be appreciated that in applying the wrap 500 to either shoulder, a person may conveniently with one hand pull the inside cinch strap from behind and about his or her body and secure this strap in place with the appropriate fastener (e.g. strap 520 and fastener parts 530 and 538) and then with this same hand pull the outside cinch strap from behind and under the arm adjoining the affected shoulder and secure this strap in place with the appropriate fastener (e.g. strap 522 and fastener parts 536 and 538). With the wrap thus securely held in place, the person may then quickly and easily adjust the tension by tightening or loosening the straps at the front pouch compartment with the cinch strap fasteners until the desired compression is achieved pressing the wrap against the shoulder.

Conclusion

A thermal wrap has been described which can be realized in various embodiments and which is useful for many applications. It embodies new structural arrangements and principles of operation which provide great improvement over the prior art thermal wraps.

Although the description of this invention has been given with reference to a particular embodiment, it is not to be construed in a limiting sense. Many variations and modifications of the invention will now occur to those skilled in the art. For a definition of the invention, reference is made to the appended claims.

What is claimed is:

1. A thermal ankle wrap for application to an ankle of a person, comprising: first and second flexible elastic cloth members co-operatively defining a flexible elastic pouch adapted to receive a thermal medium and be wrapped about a lower leg region and an ankle and an upper foot region of a person, one of said cloth members including a first flexible elastic border portion extending along one lateral side of said pouch and a second flexible elastic border portion extending along an opposite lateral side of said pouch, said border portions adapted to be brought together in an overlapping relationship at a first location behind said lower leg region and at a second location under said upper foot region when said pouch is wrapped about said lower leg region and said ankle and said upper foot region, a gap in each of said border portions, said gaps co-operatively defining an opening in said border portions between said first and second locations adapted to receive the heel of said foot when said border portions are brought in to said overlapping relationship at said first and second locations, a first wrap fastener for fastening said border portions together in said overlapping relationship at said first location whereby an upper region of said pouch is adapted to be held against said ankle with an adjustable tension force in said first wrap fastener, a second wrap fastener for fastening said border portions together in said overlapping relationship at said second location whereby a lower region of said pouch is adapted to be held against said ankle with an adjustable tension force in said second wrap fastener independent of that applied by said first wrap fastener, an elastic cinch strap secured to an upper corner of one of said border portions and adapted to wrap about said lower leg region at a location above said ankle, a cinch strap fastener for fastening said cinch strap to an upper transverse margin of said pouch after said cinch strap has been wrapped about said lower leg region, said cinch strap fastener having first and second parts, said first part secured to said upper transverse margin of said pouch along the length thereof, said second part secured to said cinch strap and adapted to fasten to said first part whereby said cinch strap is adapted to hold said upper transverse margin of said pouch against said lower leg region at a location above said ankle with an adjustable tension force independent of that applied by said first and second wrap fasteners, an elastic tension strap secured to one of said border portions at a location below the gap in this said one border portion and adapted to extend diagonally across and over said pouch to said upper transverse margin of said pouch, and a tension strap fastener part secured to said tension strap for fastening said tension strap to said first part of said cinch strap fastener whereby said pouch is adapted to be held by said tension strap against said ankle with an adjustable tension force independent of that applied by said wrap fasteners and said cinch strap.

* * * * *